United States Patent [19]

Cocking et al.

[11] Patent Number: 4,863,863

[45] Date of Patent: Sep. 5, 1989

[54] METHOD OF PRODUCING SOMATIC HYBRIDS OF THE GENUS LYCOPERSICON

[75] Inventors: Edward C. D. Cocking, Woodthrope; John B. Power, Bramcote; Ahmed M. Kinsara, Nottingham, all of England

[73] Assignee: DNA Plant Technology Corporation, Cinnaminson, N.J.

[21] Appl. No.: 833,738

[22] Filed: Feb. 26, 1986

[51] Int. Cl.$^4$ .................. C12N 15/00; C12N 5/00
[52] U.S. Cl. .................. 435/172.2; 435/240.47; 435/240.49; 435/240.51
[58] Field of Search .................. 435/240, 241, 172.2, 435/240.47, 240.51; 435/240, 241, 172.2, 240.47, 240.51

[56] References Cited

PUBLICATIONS

O'Connell et al., 1985, Theor. Appl. Genet. 70: 1–12.
Niedz et al., 1985, Plant Science 39: 199–204.
Zapata et al., 1977, Plant Sci. Lett. 8: 119–124.
Shepard et al., 1983, Science 219: 683–688.
Adams et al., 1985, Plant Science 40: 209–219.
Kut et al., 1982, In Vitro 18(7): 593–598.
Tan et al., 1987, Plant Science 49: 63–72.
Hassanpour-Estahbanati et al., 1985, J. Plant Physiol. 121: 171–174.
Haberlach, G. T. et al., "Isolation, Culture and Regeneration of Protoplasts from Potato and Several Related Solanum Species", *Plant Science*, 39: 67–74, 1985.
Handley, L. W. et al., "Somatic Hybrid Plants Between *Lycopersicon Esculentum* and *Solanum Lycopersicoides*", *Theor. Appl. Genet.*, 71: 691–697, 1986.
Kut, S. A. and Evans, D. A., "Plant Regeneration from Cultured Leaf Explants of Eight Wild Tomato Species and Two Related Solanum Species", In Vitro, 18(7): 593–598, 1982.
Kinsara, A. et al., "Somatic Hybrid Plants of *Lycopersicon esculentum* Mill and *Lycopersicon peruvianum* Mill", *J. Plant Physiol.*, 125: 225–234, 1986.

Primary Examiner—Charles F. Warren
Assistant Examiner—David T. Fox
Attorney, Agent, or Firm—Pennie & Edmonds

[57] ABSTRACT

Somatic hybrid plants of the genus Lycopersicon are produced by fusion of protoplasts of two species, one of which cannot be regenerated from protoplasts. This procedure enables the introduction of certain desirable traits of wild-type members of the genus into cultivated tomato species which do not regenerate from protoplasts.

4 Claims, 4 Drawing Sheets

METHOD OF PRODUCING SOMATIC HYBRIDS OF THE GENUS LYCOPERSICON

BACKGROUND OF THE INVENTION

This invention relates to a method of production a somatic hybrid of two species in the genus Lycopersicon.

The introduction of certain desirable traits of wild members of the genus Lycopersicon, such as plant habit, insect and disease resistance and high carotene and vitamin C content of the fruit, into cultivated tomato *L.esculentum* is restricted since the opportunity for gene flow between the cultivated tomato and its wild relatives is curtailed by interspecific incompatibilities.

Considerable effort has also been directed towards the regeneration of plants from protoplasts in tomato but this seems to be variety dependent and to occur with highly variable results.

An object of this invention is to provide an method of producing a somatic hybrid in the genus Lycopersicon.

Preferably, one species is the wild species *Lycopersicon peruvianum* which is capable of regeneration from protoplasts.

One desirable hybrid which can be produced by the method of this invention is the cross of *L. peruvianum* with the cultivated tomato *L.esculentum* which is not capable of regeneration from protoplasts.

BRIEF DESCRIPTION OF THE INVENTION

This invention relates to a method of producing a somatic hybrid plant of a wild species and a cultivated species of the genus Lycopersicon, comprising fusing protoplasts of two species, at least one of which being incapable of regeneration from protoplasts, and recovering a hybrid plant from fused protoplasts under selective regeneration conditions wherein the wild species is capable whilst the cultivated species is incapable of regeneration.

DETAILED DESCRIPTION OF THE DRAWINGS

Figure 1:
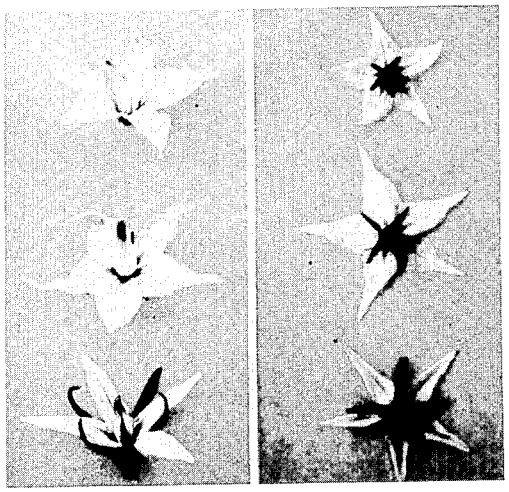

FIG. 1 is a photograph illustrating various features of a somatic hybrid and the two parental lines from which the hybrid was formed.

FIG. 1

Upper: Flower of (left to right), *L. esculentum*, the somatic hybrid and *L. peruvianum*. Note the inserted stigma arrangement of *L. esculentum* and the somatic hybrid, whilst for *L. peruvianum* it is exerted.

Lower: Underside of flowers showing difference in petal and sepal size. (⅔ actual size).

Figure 2:
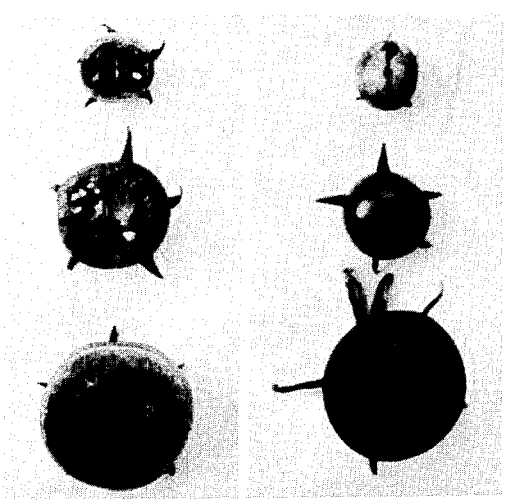

FIG. 2 is a photograph illustrating the fruit of the somatic hybrid and the fruit of the two parental lines from which the hybrid was derived.

Upper: Immature fruit of (left to right) *L. esculentum*, the somatic hybrid and *L. peruvianum* showing normal seeding development in all cases.

Lower: Fruits at maturity. The distinctive stripe on the fruit of *L. peruvianum* is absent in *L. esculentum* and the somatic hybrid. (⅔ actual size).

Figure 3:
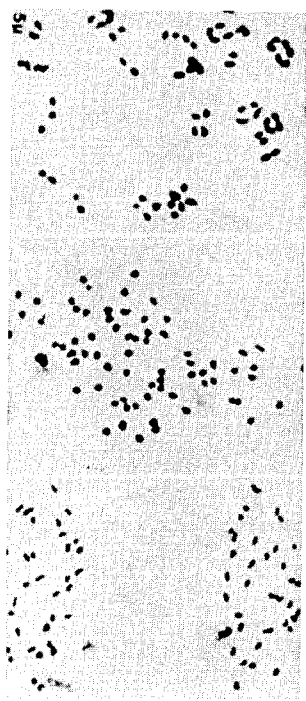

FIG. 3 is a photomicrograph of the chromosomes of the hexaploid somatic hybrid (6n=72)

Upper: Variable multivalent pattern at diakinesis
Middle: Chromosomes at Metaphase 1
Lower: Separation of chromosome (36-36) to the poles at Anaphase 1.

Figure 4:

FIG. 4 shows the isoelectric focusing of fraction 1 protein for the small (nuclear) subunit of the somatic hybrids (channels 1-8), a physical mix of extracts (channel 9), *L. peruvianum* (channel 10) and *L. esculentum* (channel 11). The arrowed bands are mutually exclusive for the two parent species and are both present in somatic hybrids and the physical mix.

DETAILED DESCRIPTION OF THE INVENTION

In general, the method of this invention enables the somatic hybridisation of species which do not regenerate from protoplasts, providing the other species involved in the cross is capable of regeneration in this manner. For example, the inability to recover whole plants from protoplasts of *L.esculentum* c.v. Ailsa Craig is advantageous in this invention as it forms the basis of selection for somatic hybrid plants following fusion with *L. peruvianum*, the latter being capable of efficient regeneration from protoplasts. The other component of the selection procedure described here, for the somatic hybridisation of *L.esculentum* with *L.peruvianum*, was based on the ability to distinguish, at the morphological level, regenerated shoots of somatic hybrids from those of *L. peruvianum* regenerating alongside.

The process of the invention may be applied to the hybridisation of cultivated non-regenerating species with other wild-type species. The skilled artisan may easily select the appropriate species for fusion by merely consulting the relevant literature in the field, for example it has been reported by Haberloch G. T. et al. (*Plant Science* 39: 67-74 (1985)) that *Solanum pennelii* (subsequently reclassified as *Lycopersicon pennellii*) is capable of regeneration from protoplasts.

Alternatively, it is possible by the mere expedient of testing from protoplast regeneration in the species of interest by employing the protoplast regeneration techniques disclosed herein. Further, it appears that the ability (or inability) of a species to regenerate from leaf explants is, to at least a first approximation, an indicator of probability of success in protoplast regeneration. Thus, data relating to regeneration from leaf tissue such as reported by Kut S. A. and K.A. Evans (In Vitro 18(7): 593-598 (1982)) can be used to advantage by the skilled artisan as sources of species, upon empirical verification in the specific conditions employed by the artisan, for practicing this invention.

The invention will now be described, by way of illustration, in the following example.

EXAMPLE

Experimental Protocol

Protoplast Isolation

Seeds of tomato, *L.esculentum* cv. Ailsa Craig (Charvil Farm, Charvil, Reading, U K.) and *L.peruvianum*, Miller S37/68 (accession S37/68, Botanic Gardens, University of Birmingham, Birmingham, U.K.) were germinated in Levington soil-less compost and seedlings grown in the greenhouse with an illumination of 10,000 lux provided by cool-white fluorescent tubes (Thorn) Plants were maintained with a 16 hour day length with a day/night temperature of 25/22°C. The accession line of *L. peruvianum*, was a partially self fertile form, maintained by sibbing, originally collected from Province Canta, Department Lima, Peru at an altitude of 1450m. Collection and authentication was by Professor J.G. Hawkes in 1964 (collection no. 2459).

*L. esculentum* (leaf mesophyll)

Fully expanded leaves from 19–25 day-old plants were surface sterilized in 8% (v/v) Domestos solution (Trade Mark, Lever Bros Ltd U.K.) for 25 min followed by 5 washes in sterile tap water. The lower leaf epidermis was removed by peeling and leaflets floated, abaxial surface down, on a salts medium (CPW) with 9% (w/v) mannitol (CPW9M). After 1 hour, the medium was removed and replaced with a filter-sterilized enzyme solution which consisted of 1.75% (w/v) Meicelase P36 (Meiji Seika Kaisha Ltd., Japan); 0.15% (w/v=Macerozyme R10 (Yakult Biochemicals Co. Ltd., Japan); 0.15% (w.v) Driselase (Kyowa Hakko Kogyco Co. Ltd , Japan); antibiotics: ampicillin (499 mg/1), tetracyclin (10 mg/1) and gentamycin (10 mg/1) in CPW9M medium (pH 5.8). Incubation was static, for 15 hours, in the dark at 27°C. Digested leaf pieces were gently squeezed to release protoplasts which were washed once, in CPW9M medium, by resuspension and centrifugation (100g, 5 min). The supernatant was finally removed and the protoplasts resuspended in CPW salts medium with 21% (w/v) sucrose (CPW21S). Following centrifugation (129g, 10 min), viable protoplasts were collected at the surface, washed once in CPW9M medium and resuspended, prior to fusion, in the same medium at a density of $4 \times 10^5$/ml.

*L. peruvianum* (suspension culture)

Cell suspension cultures of *L. peruvianum* were established from calli derived from 14 day-old hypocotyl explants grown on MS medium supplemented with 3% (w/v) sucrose, 0.8% (w.v) agar (Sigma) plus naphthalene acetic acid (2 mg/1) and 6-benzylaminopurine (0.5 mg/1), pH 5.6 (MSP1 medium). Suspension cultures were initiated and maintained in liquid MSP1 medium on a rotary shaker (80 cycles/min) at 25° with a continuous illumination of 100 lux. Cells were subcultured every 7 days and 4 days after subculture and converted to protoplasts by transfer to an enzyme mixture containing 2% (w/v) Rhozyme (Rohm and Haas Co., Philadelphia, U.S.A.); 2% (w/v) Meicelase P; 0.03% (w/v) Macerozyme R10 in CPW salts with 13% (w/v) mannitol (CPW13M) (pH 5.8). Incubation was for 16 hours on a rotary shaker (30 cycles/min) with an illumination of 100 lux at 25°C. After incubation, protoplasts, together with the enzyme solution, were passed through a 64 nylon sieve. Protoplasts were centrifuged (100g, 5 min) and the enzyme supernatant replaced by CPW21S medium. Protoplasts were washed as described previously and resuspended in CPW9M medium at a density of $4 \times 10^5$/ml.

On occasions and in order to monitor heterokaryon formation fluorescein isothiocyanate (FITC) was added to the *L. peruvianum* cells in the enzyme solution This was achieved by adding 50 ml of FITC stock (5 mg (w/v) in 1 ml acetone) to 20 ml of enzyme solution prior to incubation.

Fusion of protoplasts

Leaf protoplasts of *L. esculentum* and cell suspension protoplasts of *L. peruvianum*, both a density of $4 \times 10^5$/ml in CPW9M medium, were mixed 1:1. Aliquots (0.3 ml) of the mixture were placed in 5 cm petri dishes (Nunc, Intermed, Denmark) and the protoplasts allowed to settle on to the bottom of the dish for 10–15 min. Three drops of a PEG fusion solution (39% (w.v) polyethylene glycol, MW 6000 (Koch-Light) 2.36% (w/v) Ca (NO$_3$)$_2$.4H$_2$O and 9% (w/v) mannitol, pH 5.8) were added to the settled protoplasts in such a way that the drops gradually coalesced over a 25–30 min period. The PEG fusion solution was carefully removed, leaving the protoplasts undisturbed, and replaced by 0.5 ml of a high pH/Ca$^{++}$fusion solution (0.74% (w/v) CaCl$_2$.2H$_2$O; 9% (w/v) mannitol buffered at pH 10.4 using glycine/NaOH. After a further 10 min the high pH/Ca$^{++}$solution was removed and the protoplasts washed twice with 0.5 ml aliquots of CPW13M medium containing 0.74% (w.v) CaCl$_2$.2H$_2$O. Each washing stage was extended for 10 min whereupon the protoplasts were washed 2–3 times with 0.5–1.0 ml aliquots of culture medium. The culture medium (TCM) consisted of a 1:1 mix of MSP1 medium with 9% (w/v) mannitol and R9 medium also with 9% (w/v) mannitol, pH 5.8.

Control dishes were also prepared for both parental protoplasts (unfused and subsequently mixed or plated separately) in TCM medium at a final density of $4 \times 10^5$ protoplasts/ml.

Culture of Protoplasts

Protoplasts from the fusion treatments were maintained in TCM medium (with 9% (w/v) mannitol) (4 ml of medium per dish) at 30o in the dark for 1 week, whereupon the dishes were transferred to give a continuous illumination of 4000 lux (daylight fluorescent tubes) at 25°C. After 1 month, small green colonies appeared in some of the dishes whereupon the mannitol concentration was progressively reduced, at 2 weekly intervals, by the addition, to each dish, of 0.5 ml TCM medium with 6% (w/v) mannitol, 3% (w.v) mannitol and finally no mannitol.

Two weeks after the final dilution, calli were large enough to be transferred to the shoot regeneration medium which consisted of MS medium with 1 mg/1 zeatin as the sole growth regulator (MSZ) and 0.8% agar (pH 5.8). After 4 weeks small shoots, still attached to the callus, were transferred to fresh MSZ medium with a continuous illumination of 500 lux (daylight fluorescent tubes). When large enough to handle, the shoots were excised from the callus and rooted (after 3 weeks) and MS medium lacking growth regulators (MSO) but with 0.6% agar.

It was at this stage that selected plants were transferred to pots, with soil-less compost, and maintained at high humidity for 5 days before final transfer to the open greenhouse. Plants were raised to flowering under an illumination of 10,000 lux, 16 hour day length and a temperature regime of 25° C. day/20° C. night.

Analysis of Regenerated Plants a). Morphological Comparison

A detailed comparison of morphology was carried out for *L. esculentum, L peruvianum* and the putative somatic hybrids. Characteristics distinguishing the two parent species were specifically stem, leaf, inflorescence, fully expanded flower, sepals, stigma (inserted or exerted) and fruit morphology. Hybridity of the regenerated plants was expected to be expressed in relation to one or more of the aforementioned features since this was the situation for previously prepared sexually produced hybrids.

b). Chromosomal Analysis

Both mitotic and meiotic analyses were carried out on selected regenerated plants and plants of the two parents in order to determine chromosome number and pairing behavior. For mitotic studies root tips were pretreated with 0.2% (w/v) colchicine solution (12 hours), fixed in acetic alcohol (glacial acetic acid/ethanol, 1:3), hydrolysed in 5N HCl for 10 min and finally squashed in 2% aceto-orecein. Meiotic analysis was achieved by fixing young flower buds in acetic alcohol and squashing the anthers in 2% aceto-carmine. Slides were temporarily sealed with wax and photomicrographs taken.

Cells of *L. peruvianum*, grown in suspension culture for protoplast isolation, were fixed and examined chromosomally.

c). Pollen Viability

This was determined by staining mature pollen in an acetocarmine/glycerine mixture (1:1). Round and intensely stained grains were deemed viable.

d). Fraction 1 Protein Analysis

The parent species and the selected plants obtained from the fusion experiments were analysed for their Fraction 1 protein profiles.

(i) Extraction of protein:

Fully expanded leaves (1 gm fresh weight), from the upper part of the plant, were ground in ice in a mortar using 1 ml buffer (0.05M Tris-HCl, pH 6.8, 18% (v/v) glycerol, 0.5% 2-mercaptoethanol and 1 mg/100 ml Leupeptin). Leaf extracts were obtained by squeezing the ground material through a muslin cloth and 0.1 gm (per ml of extract) of Sephadex (G 50-80) added. The mixture was centrifuged (13,000 g 10 min) and the supernatant was used for protein analysis.

(ii) Polyacrylamide gel electrophoresis:

A vertical electrophoresis unit (Model 2001,LKB) was used with a discontinuous buffer system and stacking gel above the separation gel. The separation gel, about 10 cm in height, contained a final concentration of 6% acrylamide and 0.375 Tris-HCl (pH 8.4). The stacking gel about 2.5 cm in height, was layered over a separation gel which consisted of 3% acrylamide, and 0.125M Tris-HCl (pH 6.8). The electrode buffer contained 0.025M Tris-HCl and 0.129M glycine (pH 8.3). The protein sample (50-100 microlitre approx. 70 microgram protein) was loaded in each well and the gels run with a constant current of 10 milliamps for 18 hours. Fraction 1 protein was visualised by staining for total protein for 5 min in a solution containing 0.1% Coomassie Brilliant Blue 50% (v/v) methanol and 10% (v/v) acetic acid. The gels were destained in a solution of 5% (v/v) methanol and 10% (v/v) acetic acid for 10 minutes. The position of fraction 1 protein was evident by its slow migration and high staining intensity.

(iii) Isoelectric focusing of the small subunit polypeptides of fraction 1 protein:

The fraction 1 protein band, cut from the gel, was immediately placed in a freshly prepared solution of 8M urea, 0.5% dithiothreitol, 5% (wv)sucrose, and 2.5% (vv) Ampholine (LKB), (pH 3.5-10) and incubated in the dark for 30 min at room temperature.

Isoelectric focusing was performed on a 1.5 mm thick slab gel, using a LKB 2117 multiphore electrophoresis apparatus. Gels contained a final concentration of 4.85% (w/v) acrylamide, 0.15% (w/v) bisacrylamide, 8M urea, 2% (v/v) Ampholine (LKB) pH range 5-8 and 0.75% (v/v) Ampholine (LKB) pH range 3-10. Polymerisation of the gel was completed by the addition of TEMED (N,N,N,N-tetramethyl ethylenediamine) (final conc. of 0.1% (v/v)) and freshly prepared ammonium persulphate solution (final conc. 0.02%). Gels were prefocused for 1.5 hours form 0 to 1200v at a maximum current of 20 milliamps. Gel pieces containing disassociated fraction 1 protein, were then loaded onto the surface of the prefocused gel and were run for 2 hours at 15°C. at a maximum current of 20 milliamps with a final constant voltage of 1200v.

(iv) Location of the polypeptides of fraction 1 protein:

The gels were fixed overnight in a solution of 12% (w/v) trichloroacetic acid and 3.5% (w/v) sulphosalicylic acid, followed by staining, at 60°C., 30 min., in a solution of 0.15% (w/v) PAEG Blue 83 (BDH) in 25% (v/v) ethanol and 8% (v/v) acetic acid. Gels were destained several times with several changes of 25% (v/v) ethanol and 8% (v/v) acetic acid mixture.

RESULTS

In TCM medium unfused protoplasts of *L. peruvianum* entered division to form large green colonies whereas protoplasts of *L. esculentum* did not grow beyond the small cell colony stage. TCM medium therefore proved suitable as a half selection for somatic hybrids since protoplasts (unfused or homokaryon) of *L. esculentum* cannot give rise to callus.

Following fusion, heterokaryon frequency was 5-7% as judged by the presence of fluorescing, chloroplast-containing protoplasts. This relatively high level of heterokaryon formation was maintained for all 21 experiments based on the present protocol. Fusion treated protoplasts and heterokaryons entered division after 10 days which resulted in green colonies (3-4 mm diam.) after 2 weeks. When transferred to MSZ medium these colonies developed shoot-bearing calli after 30 days.

In 18 of the 21 fusion experiments, regenerated shoots and plantlets were similar, in terms of their morphology, to shoots of *L. peruvianum* arising in the appropriate control. A random sample of such shoots taken to maturity were *L. peruvianum* and were discarded.

However, in 3 separate experiments, some of the regenerated shoots were atypical in that they differed morphologically from those of *L. peruvianum* in relation to their stem which was stouter, less rounded leaf tips and generally darker green in appearance. All such shoots, and for all 3 experiments, were carefully maintained, grown to flowering, and subsequently subjected to further detailed analysis.

Experiment 1 gave 4 calluses, of separate origin, and a total of 11 plants (arbitrarily numbered 1, 5, 9, 15, 16, 20, 21, 22, 23, 24, 25). These plants are subsequently referred to as Group 1.

Experiment 2 gave rise to approximately 250 calli of which 6 calli produced morphologically distinct shoots. Of these 6 events, 4 calli, each with a single shoot, were maintained separately and the four plants, hereafter referred to as Group 2a were numbered 8, 10, 12, 13. The two remaining calli each gave rise to 4 shoots numbered 2, 3, 4, 6 (Group 2b) and 7, 17, 18, 19 (Group 2c).

Experiment 3 produced a few (<20) calli of which one underwent regeneration to give 2 shoots of interest (numbered 11,14), Group 3.

Identification of Somatic Hybrids a) Morphological assessment

Plants of all the groups flowered and set fruit. However, plants of Groups 2b and 2c took 6 months to initiate flowers whilst those of the other groups required only 4 months. The comparative morphology of these individuals, as shown in FIGS. 1, 2, suggested that they were hybrid in nature It was noted that the plants of Groups 2b, 2c had some features representative of both *L. esculentum* and *L. peruvianum*. Conversely, the plants of Groups 1, 2a, 3, though slightly different in relation to leaf form, had the same floral arrangement as *L. peruvianum*.

b) Cytological analysis

Mitotic and meiotic analysis of plants of both parents confirmed that they were diploid with 2n =24 chromosomes forming regular 12 bivalents at diakinesis in pollen mother cells. Cells of the suspension culture of *L. peruvianum* as used for protoplasts fusion were however predominantly tetraploid, as were all plants regenerated from the *L. peruvianum* unfused protoplast control.

Cytological analysis of the selected plants (all 3 experiments) were mostly carried out via meiotic analysis The results fall into two categories.

Tetraploids

Six plants of Group 1 (nos 1, 5, 15, 16, 21, 22) were analysed and four (1, 15, 21, 22) were tetraploid with 4n =48 chromosomes with a variable proportion of quadrivalents, bivalents and univalents at diakinesis. By metaphase I most of the quadrivalents were split into two with a regular arrangement in the equatorial plan; anaphasic separation therefore, resulted in 24–24 separation to the two poles. In rare instances 23–25 or 22–26 separation was noticed.

One plant (5) had 4n =49 chromosomes (with a 24–25 separation at anaphase) and the other (16) was 4n =47 chromosomes and invariably as 23–24 separation.

Similarly plants of Groups 2a, 3 were also tetraploid with 4n=48 chromosomes.

Hexaploids (somatic hybrids)

All plants of Groups 2b, 2c were hexaploid with 6n =72 chromosomes.

The plants exhibited a variable multivalent pattern since, at diakinesis, often a few hexavalents (chains or rings) were observed alongside pollen mother cells exhibiting a variable univalent to hexavalent proportion. However, by late metaphase the multivalents fell apart so that anaphasic cells with a 36–36 separation could be largely realized (See FIG. 3). On occasions and at low frequency, irregular separation (35–37 or 34–38) was noted. In all the plants with a 6n =72 chromosome number subsequent phases of meiosis were regular with 36 chromosomes in a high proportion of tetrad cells.

Pollen viabilities are given in Table 1 below and the figure quoted represents the percentile count for 500 pollen grains per flower and for 5 flowers per plant taken at random.

TABLE I

| POLLEN VIABILITY | |
|---|---|
| Plants species/regenerants | % viability |
| *L. esculentum* Mill. c.v. Ailsa Craig | 95.5 |
| *L. peruvianum*, Mill. | 65.3 |
| Groups 1, 2a, 3 (*L. peruvianum* 4n = 48) | 43.0 |
| Groups 2b, 2c (Somatic Hybrids, *L. esculentum* x *L. peruvianum*, 6n = 72) | 45.2 | c) Fraction 1 protein analysis

*L. esculentum* and *L. peruvianum* had identical polypeptide bands for the large (chloroplast) subunit. They were distinguishable for the small (nuclear) subunit. Both species were characterized by 3 bands in the small subunit of which 2 bands were common. The position of the third band was mutually exclusive (FIG. 4) and this enabled unambiguous identification/confirmation of hybridity to be made.

Upon analysis all plants of Groups 1, 2a, 3 were shown to be *L. peruvianum*. All plants (à total of 8) of Groups 2b, 2c exhibited an identical banding pattern to that of a physical mixture of parental protein extracts (FIG. 3). Taking into account this observation, plus the morphological data (FIG. 1) it was concluded that these plants were somatic hybrids (*L. esculentum* ⊗ *L. peruvianum*) with a 6n=72 hexaploid chromosome complement.

DISCUSSION

Somatic hybrid plants (*L. esculentum* ⊗ *L. peruvianum*) were hexaploid (6n 72), fert . and set seed upon self pollination. The ploidy level in the plants was probably attributed to the fact that *L. peruvianum*, in culture, was predominantly tetraploid, thereby following fusion, giving a somatic hybrid cell and ultimately hybrid plants composed of a tetraploid *L. peruvianum* (4n =48) and diploid *L. esculentum* (2n =24) chromosome complement. The fact that these hybrids are self fertile, set viable seed and, in preliminary experiments can be readily backcrossed to *L. esculentum*, is in contrast to the situation reported for sexually produced F1 hybrids which are frequently self-sterile and do not backcross readily.

An important aspect of the selection method was that plant regeneration in tomato was not a prerequisite. This concept should apply to other species combinations involving tomato, provided that there is an inherent regeneration capacity on the wild-type side.

Confirmation of hybridity required not only morphological comparisons to be made with the respective parents and the reported sexually produced F1 hybrids involving *L. esculentum* and *L. peruvianum*, but since different varieties and accessions of *L. peruvianum* have been used by other workers, unambiguous characterization was based on Fraction 1 protein analysis.

It was possible to distinguish between each of the two species and somatic hybrids in relation to the small (nuclear-coded) subunit of Fraction 1. Thereby nuclear hybridity was confirmed for these plants, although it was not possible to distinguish the two parent species for the large encoded (chloroplast-coded) subunit.

The somatic hybridisation of *L. esculentum* with *L. peruvianum*, incorporating a non-regenerating variety of tomato, extends the potential of this technique to include all varieties of tomato, and their ultimate hybridisation with more taxonomically distant wild-types, provided the wild types are inherently capable of regeneration.

This invention also provides the potential for the synthesis of gametosomatic hybrids in tomato, parallelling the situation in Nicotiana with the incorporation of a haploid genome from any wild-type species of Lycopersicon.

What is claimed is:

1. A method of producing a fertile somatic hybrid plant of a wild species of the genus Lycopersicon and *Lycopersicon esculentum*, comprising fusing protoplasts of two species, at least one of which being incapable of plant regeneration from protoplasts, and recovering a hybrid plant form fused protoplasts under selective regeneration conditions wherein the wild species is capable of plant regeneration whilst the cultivated species is incapable of plant regeneration.

2. The method of claim 1 wherein one species is *Lycopersicon esculentum* and the other species is *Lycopersicon peruvianum*.

3. The method of claim 1 wherein the protoplasts are fused in a polyethlene glycol fusion solution.

4. The method of claim 1 wherein the selective regeneration conditions comprise culturing in a medium for a period of time sufficient for the development of callus from the somatic hybrid and one of the fusion partners.

* * * * *